United States Patent [19]

Gentry

[11] Patent Number: 4,882,283
[45] Date of Patent: Nov. 21, 1989

[54] HEAT EXCHANGE APPARATUS

[75] Inventor: Cecil C. Gentry, Bartlesville, Okla.

[73] Assignee: Phillips Petroleum Company, Bartlesville, Okla.

[21] Appl. No.: 122,291

[22] Filed: Nov. 17, 1987

[51] Int. Cl.[4] ............................................. C12M 1/02
[52] U.S. Cl. ................................... 435/316; 435/313; 435/315; 435/287; 165/109.1; 165/1; 165/2
[58] Field of Search ........................... 165/2, 166, 142; 435/316, 315, 313, 287

[56] References Cited

U.S. PATENT DOCUMENTS

| | | | |
|---|---|---|---|
| 2,174,203 | 9/1939 | Ducellier et al. | 137/78 |
| 2,764,476 | 9/1956 | Etten | 23/285 |
| 2,875,027 | 2/1959 | Dye | 23/285 |
| 3,262,489 | 7/1966 | Fritzberg | 165/175 X |
| 3,847,750 | 11/1974 | Ridgway, Jr. et al. | 195/142 |
| 3,962,042 | 6/1976 | Malick | 195/143 |
| 3,978,918 | 9/1976 | Nagatomo et al. | 165/109 |
| 4,019,962 | 4/1977 | Allen et al. | 195/142 |
| 4,136,736 | 1/1979 | Small | 165/162 |
| 4,304,222 | 12/1981 | Novinger | 126/443 |
| 4,442,889 | 4/1984 | Müller | 165/109 R |
| 4,670,397 | 6/1987 | Wegner et al. | 435/289 |

FOREIGN PATENT DOCUMENTS

| | | |
|---|---|---|
| 1905218 | 2/1968 | Fed. Rep. of Germany . |
| 1249001 | 11/1960 | France . |
| 422571 | 7/1933 | United Kingdom . |

OTHER PUBLICATIONS

Norman L. Hurd, "Mean Temperature Difference in the Field or Bayonet Tube", IEC 38(12), 6/1946.
Perry & Green (eds), Perry's Chemical Engineers Handbook, 6th ed., McGraw-Hill, 8/1984, pp. 11–23.
D. L. Kern, Process Heat Transfer, McGraw-Hill, 5/1950, pp. 738–745.

Primary Examiner—Larry Jones
Attorney, Agent, or Firm—H. B. Woodrow

[57] ABSTRACT

A heat exchange tube formed from a sheath containing a bayonet tube all mounted on a split pipe header is especially well suited for the construction of tube bundles to be used in fermentors.

15 Claims, 7 Drawing Sheets

HEAT EXCHANGE APPARATUS

In one embodiment, the invention relates to a heat exchange apparatus. In another embodiment, the invention relates to a heat exchange process.

BACKGROUND OF THE INVENTION

In many processes using a stirred vessel, heat is transferred from the vessel fluid to a secondary fluid flowing through vertical pipes which baffle the vessel fluid. These vertical pipe-coil baffles serve as both mixing baffles, to prevent vortex formation about a rotating agitator used to stir the vessel fluid, and provide heat transfer surface area. There are numerous process applications for vertical pipe-coil baffles.

A major disadvantage to vertical pipe-coil baffles is the lack of provision for thermal expansion to accommodate larger temperature differential applications between the pipe coil fluid and the mixing vessel fluid. Thermal expansion and contraction are very significant problems where long tubes are used especially tubes arranged in a single pass tube bundle. In such tube bundles, the inlet and outlet headers are susceptible to stress cracking. Thermal expansion stresses are lower in U-tube bundles but the design is not very compact, limiting the heat transfer surface area available for a tube bundle of fixed external dimensions. "U" tube bundles also have a relatively poor heat exchange coefficient and require a complex manifold arrangement.

A tube bundle designed to overcome thermal expansion problems, especially an agitated mixing vessel, would be very desirable.

OBJECT OF THE INVENTION

It is an object of this invention to provide an apparatus especially well adapted for exchanging heat in a stirred fluid vessel.

It is another object of this invention to provide a process for indirectly exchanging heat between two fluids.

SUMMARY OF THE INVENTION

In one embodiment of the invention, an apparatus is provided for heat exchange. The apparatus comprises a vessel capable of containing a liquid. A pipe is mounted in the vessel. A partition is mounted on the inside of the pipe, dividing the inside of the pipe into a first chamber and a second chamber. A first tubular member is mounted to the sidewall of the pipe by a first end thereof. A second end of the tubular member is sealed with a closure. A second tubular member is positioned inside of the first tubular member. A first end of the second tubular member is attached to an aperture in the partition and a second end of the second tubular member is spaced apart from the closure on the first tubular member. A flow path is thereby formed from the first chamber, through the second tubular member, through an annulus between the second tubular member and the first tubular member, and into the second chamber. A fluid inlet means extends through the sidewall of the vessel and is connected to the first chamber. A fluid outlet means extends to the sidewall of the vessel and it is connected to the second chamber. The arrangement is compact, simple, and characterized by a high heat transfer coefficient, and it also operates free of thermally induced stresses.

In another embodiment of the invention, there is provided a method for circulating a heat exchange fluid. The heat exchange fluid is introduced into a vessel through an inlet means which extends through the vessel wall. The heat exchange fluid is distributed from the inlet means into a plurality of first heat exchange tubes each having a first end and a second end and connected by the first end to the inlet means. The heat exchange fluid flows from the first end of the plurality of first heat exchange tubes to the second end of the plurality of first heat exchange tubes. At the second end of the plurality of first heat exchange tubes, the heat exchange fluid flows into the first end of a plurality of second heat exchange tubes each concentrically positioned around a first heat exchange tube. The heat exchange fluid then flows from the first end of the plurality of second heat exchange tubes along a plurality of annuli defined between the first heat exchange tubes and the second heat exchange tubes to a second end of the second heat exchange tubes at which point the heat exchange fluid is discharged from the second heat exchange tubes and is collected in an outlet means which extends through the vessel wall for withdrawal from the vessel.

DETAILED DESCRIPTION OF THE INVENTION

Figure 4:
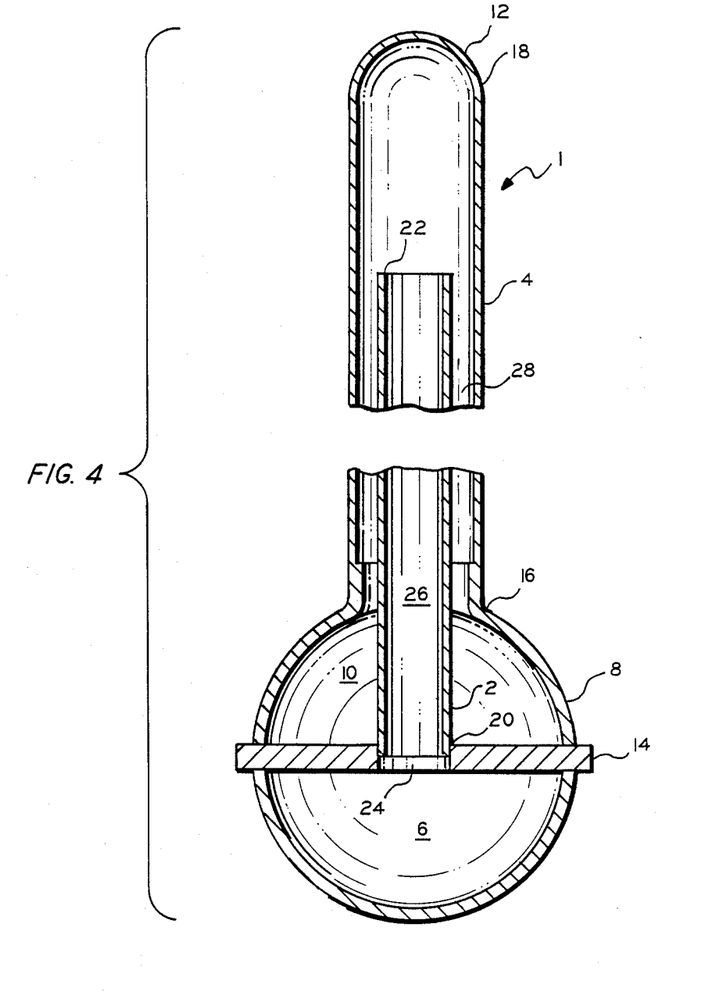
FIG. 4 is a cross-sectional view of a portion of the apparatus embodying certain features of the present invention as would be seen when viewed along the lines indicated in FIG. 1.

With reference to FIG. 4, the invention includes a plurality of bayonet tubes 2 and sheath 4 together forming a bayonet tube assembly designated generally by 1. The bayonet tube 2 opens into an inlet chamber 6 of a split pipe manifold 8. The sheath 4 opens into an outlet chamber 10 of the split pipe manifold 8. Fluid enters the inlet manifold chamber 6 and is distributed to the inside of the bayonet tube 2. The bayonet tubes 2 are installed within the larger diameter sheath tubes 4. The entering fluid passes upward through the bayonet tube 2, reverses flow direction in a weld cap 12 on the end of the sheath tube 4 and flows downwardly in the annular space 28 between the bayonet tubes 2 and sheath tubes 4. Any thermal expansion between the sheath tube 2 and bayonet tube 4 takes place in the weld cap region, with no thermal stresses generated.

The bayonet tube 2 and sheath 4 can be positioned in any desired direction. Preferably, the bayonet tube and sheath are positioned vertically upwardly or vertically downwardly, preferably vertically upwardly where two-phase fluid is to be carried. The split pipe manifold 8 can be characterized as a pipe having a partition 14 mounted therein. Preferably, the partition 14 is mounted diametrically across the pipe and divides the pipe into a first chamber which serves as the inlet chamber 6 and a second chamber which serves as the outlet chamber 10. The sheath tube 4 can be described as a first tubular member having a first end 16 which is attached to the pipe and a second end 18 to which is mounted a closure such as the weld cap 12. The bayonet tube 2 can be formed by a second tubular member having a first end 20 attached to the partition 14 and a second end 22 which is spaced apart from the end closure on the first tubular member. The first end of the second tubular member is mounted in an aperture 24 in the partition plate 14 so that a flow path is formed from the first chamber 6, through the inside 26 of the second tubular member, and then through an annulus 28 defined between the outside of the second tubular member and the inside of the first tubular member and into the second chamber 10.

Figure 1:
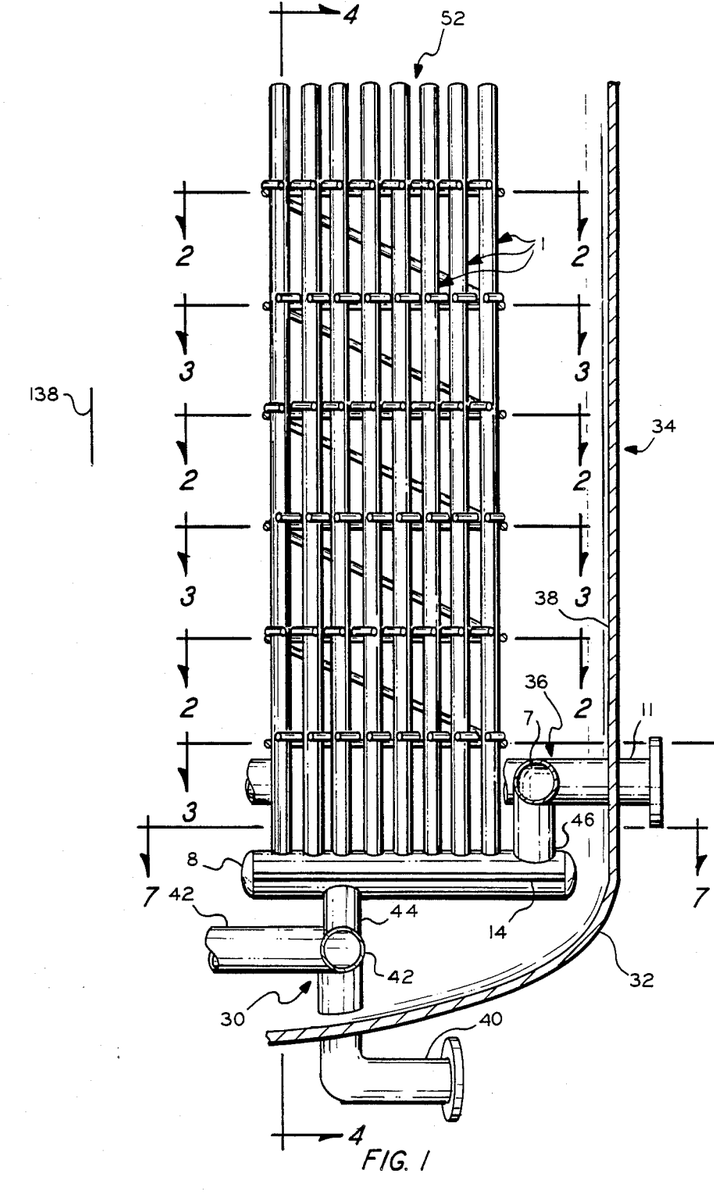
FIG. 1 is a view taken in partial cross-section of a bundle of tubes which embody certain features according to the present invention.

With reference to FIG. 1, a fluid inlet means 30 extends through a sidewall 32 of a vessel 23 and is connected to the first chamber. A fluid outlet means 36 extends through the sidewall 32 of the vessel 34 and is connected to the second chamber.

Figure 8:
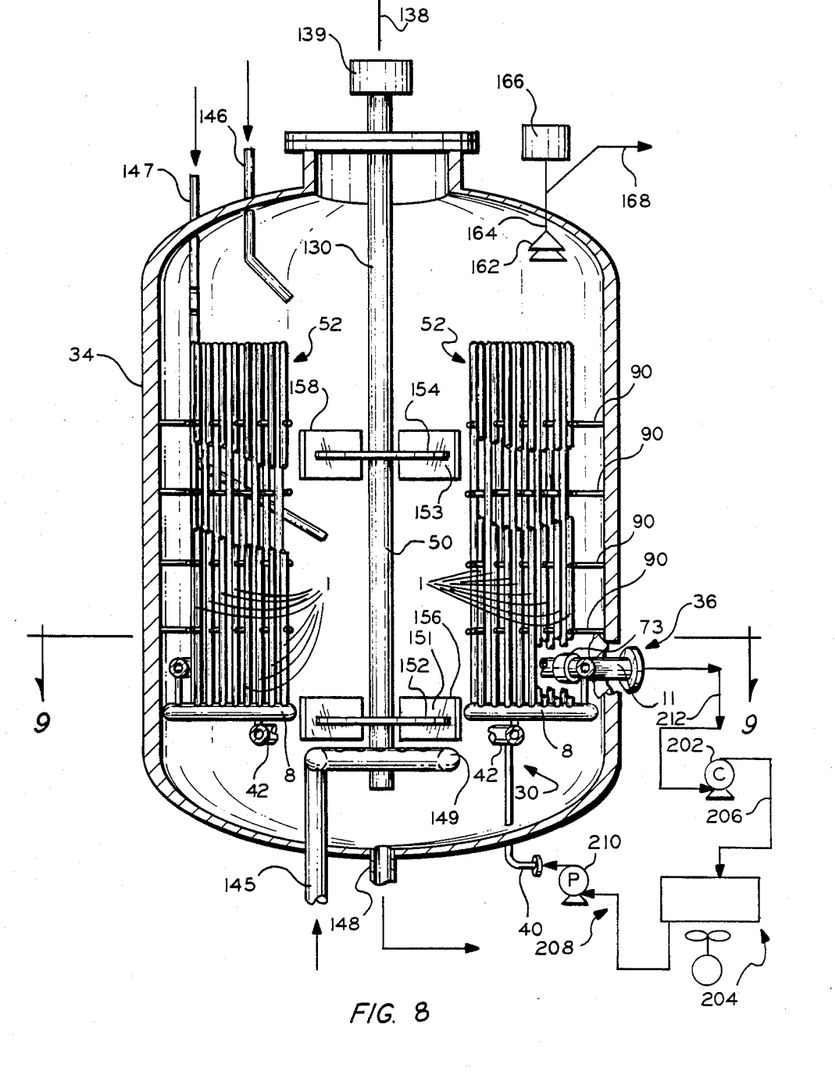
FIG. 8 is a cross-sectional view, partly schematic, illustrating additional features of an embodiment of the invention.

In a preferred embodiment of the invention, the vessel 34 is capable of containing a fluid, usually a liquid or liquid vapor mixture, and can be constructed similar to the vessel shown in FIG. 8, for example. A portion of the sidewall 32 forms a generally cylindrical inside surface 38 of the vessel 34. The generally cylindrical inside surface 38 is symmetrically positioned around a longitudinal axis 138 of the vessel 34. (See FIGS. 1 and 8). The general dimensions of the vessel 34 will usually be selected so that the ratio of length to diameter will generally be in the range of from about 0.1:1 up to about 10:1. Preferably, the ratio of length to diameter when the vessel is to be used for a fermentation process as hereinafter described will range from about 0.3 up to about 5:1, with the ratio of length to diameter most preferably falling in the range of about 1:1 up to about 4:1.

As shown in FIG. 1, the fluid inlet means 30 preferably comprises a feed pipe 40 extending through the sidewall 32 of the vessel 34. The feed pipe 40 is preferably connected to a curved supply pipe 42. The supply pipe 42 extends preferably generally circumferentially around and spaced apart from the inside sidewall of the vessel 34. The supply pipe 42 is preferably connected to the first chamber 6 by a riser feed pipe 44. In a fermentor, a plurality of split pipe manifolds will usually be utilized and thus a plurality of riser feed pipes will connect each supply pipe 42 with the plurality of split pipe manifolds 8. See FIG. 9. In a preferred embodiment, the riser feed pipes 44 are connected to an inside end portion of the split pipe headers 8.

The fluid outlet means 36 preferably comprises a first exhaust pipe 11 which extends through the sidewall 32 of the vessel 34. See FIG. 1. The exhaust pipe 11 is preferably connected to a curved collection pipe 7 which extends generally circumferentially around the inside of the vessel 34 at a position spaced apart from the sidewall 32, preferably positioned between one or more bayonet tube assemblies 1 and the generally cylindrically portion 38 of the sidewall 32. A riser exhaust pipe 46 connects the outlet chamber 10 of the split pipe manifold 8 with the curved collection pipe 7. In a fermentor, many split pipe manifolds will generally be present and thus an equal number of riser pipes 46 will be utilized.

In a preferred embodiment of the invention, the heat exchange fluid is a refrigerant, preferably ammonia. With refernece to FIG. 8, a gas compressor 202 is positioned to draw fluid from fluid outlet 11. A condenser 204 is positioned to cool an exchaust stream from the gas compressor 202. A conduit means 206 connects the gas compressor 202 with the condenser 204. A conduit means 208 connects the condenser 204 with the fluid inlet means 30. Preferably, the conduit means 208 includes a pump 210 to provide for liquid flow from an outlet of the condenser 204 to the bayonet tube assemblies 1. A conduit means 212 preferably connects the fluid outlet means 11 with the compressor 202.

Figure 9:
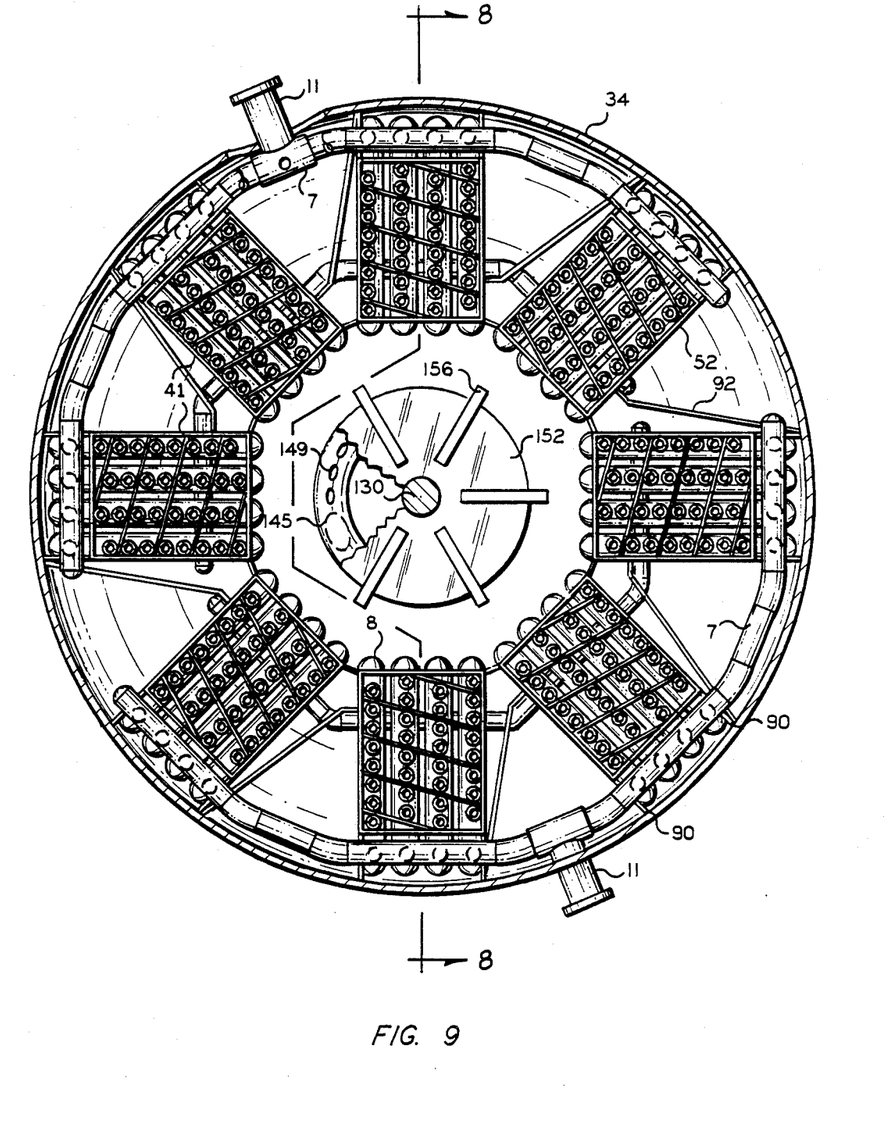
FIG. 9 is a cross-sectional view of the device shown in FIG. 8 taken in the plane of the indicated lines.

In a preferred embodiment of the invention, a plurality of the split pipe manifolds 8 are mounted in the vessel 34 in an orientation which is generally radially oriented with respect to the longitudinal axis 138 of the vessel 34. See FIG. 9. Preferably, the split pipe manifolds 8 are grouped in sets of from about 3 to about 12 forming the bundles 52 and are aligned on chords which pass across the vessel near a vessel diameter. The tube assemblies 1 extend from each plurality of split pipe manifolds 8 as a bundle of generally parallel tubes which are preferably oriented generally parallel to the longitudinal axis of the vessel. The split pipe manifolds 8 are preferably positioned in a lower portion of the vessel and the tube assemblies 1 extend upwardly therefrom. See FIG. 1. The tube assemblies 1 in adjacent rows of tubes are displaced so that the tubes in the tube bundle are laid out in a triangular pitch. See FIGS. 2 and 3. The individual tube assemblies 1 are supported by the rods of a pair of rod baffles formed from a first rod baffle 48 and a second rod baffle 50. Preferably, each of the rod baffles 48 and 50 contain sufficient rods so that each tube assembly 1 in the tube bundle 52 is supported on two sides by each rod baffle 48 or 50 and the pair of rod baffles 48 and 50 together support all four sides of each tube assembly 1 thereby providing each tube 1 of the bundle 52 with radial support. If desired, the rods of each rod baffle can be positioned between alternative tube rows as shown in FIG. 9 for example, in which event four rod baffles are required to provide each tube bundle with radial support. This embodiment causes less pressure drop for longitudinally flowing fluids. It is important that rods 54 of the rod baffles 48 and 50 be sized to touch and support the tubes on each side of the lane through which the rods are positioned. The required cross-sectional dimension of the rods depends on the cross-sectional dimension of the lanes through which the rods are positioned. The rods can have any desired cross-sectional shape such as round, elliptical, square or rectangular for example. It is preferred however, in order to provide point contact between the rod and tube that the rods be round. Point contact between the tube and rod facilitates cleaning of the tube bundle, an important consideration where the bundle is to be used to cool a fermentation process as hereinafter described.

Figure 6:
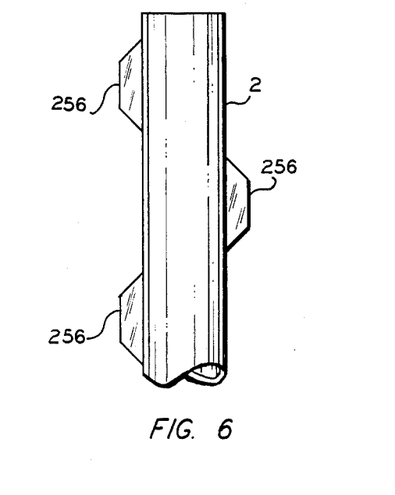
FIG. 6 is a pictorial representation of a portion of the apparatus shown in FIG. 4.
Figure 7:
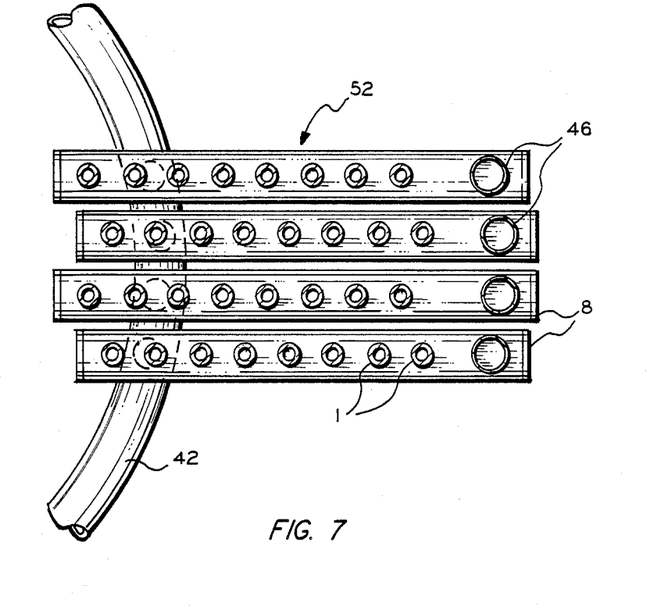
FIG. 7 is a cross-sectional view of a portion of the apparatus as shown in FIG. 1 when viewed along the indicated lines.

The rod baffles are designed to prevent tube collisions and damage to the tube bundle when in use. The rod baffles also prevent tube movement which can result in fatigue failures at sheath to manifold welds. To prevent damage from internal collision between the bayonet tube 2 and sheath 4 it is desirable to position spacers 256 between each bayonet tube 2 and each sheath 4. See FIG. 6. Preferably, the spacers 256 are welded onto an exterior surface of the bayonet tube 2. Preferably the spacers 256 are somewhat elongated and extend longitudinally along the exterior surface of the bayonet tube 2 in order to reduce flow impedance. In a preferred embodiment, spacers 256 are formed from welding rods sized to support the bayonet tube 2 in the sheath 4. The spacers 256 are preferably affixed on the exterior of the surface of the bayonet tube 2 to provide radial support of the tube 2 inside the sheath 4. Thus, there is preferably at least 3 point support of each bayonet tube 2 inside each sheath 4 by the spacers 256.

Figure 2:
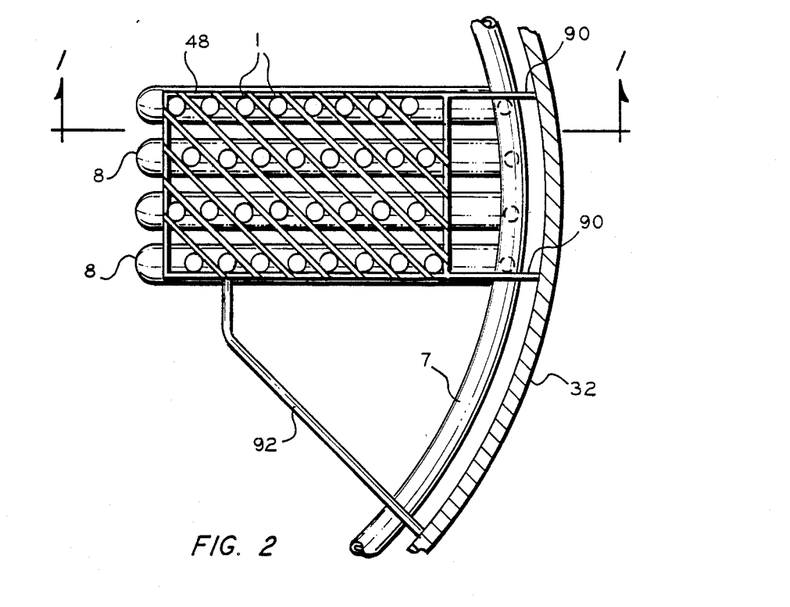
FIG. 2 is a partly schematic representation of the apparatus as would be seen in FIG. 1 when viewed along the indicated lines.
Figure 3:
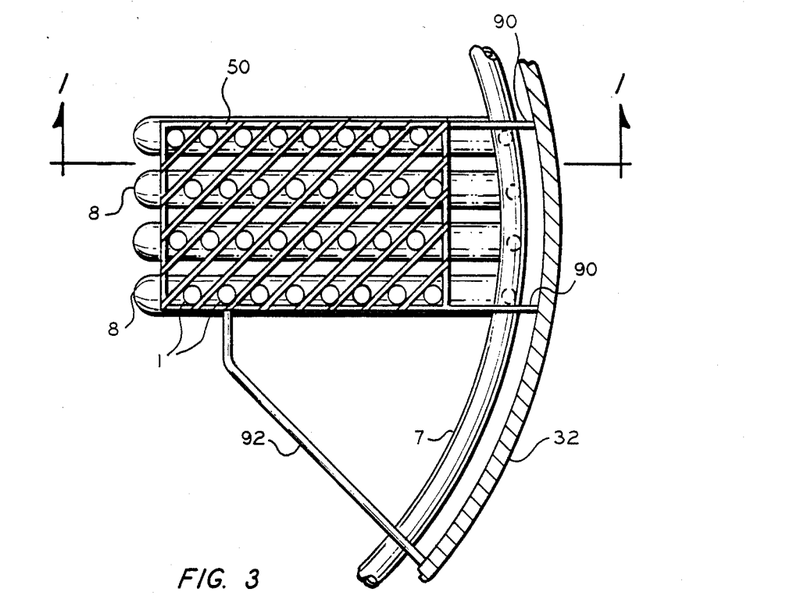
FIG. 3 is a partly schematic representation of the apparatus as would be seen in FIG. 1 when viewed along the indicated lines.
Figure 5:
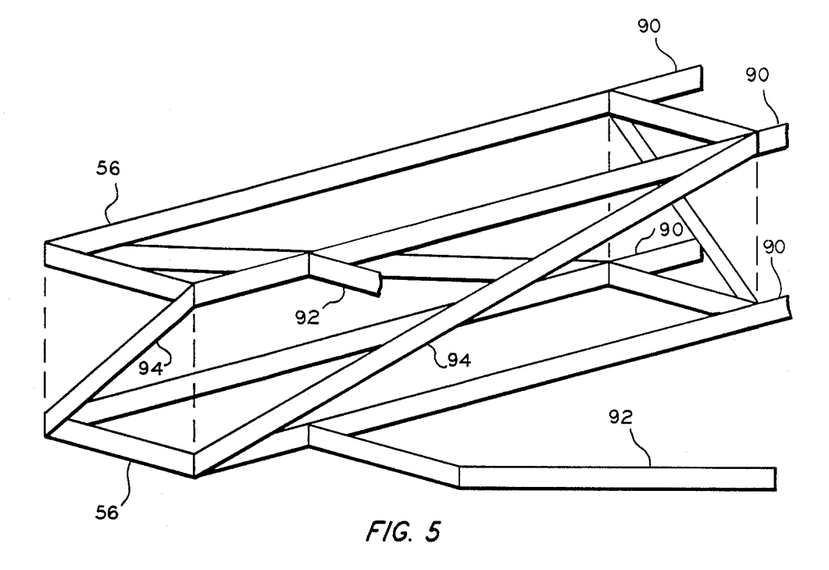
FIG. 5 is a pictorial representation of a portion of the apparatus of FIG. 1.

With reference to FIG. 5 and FIG. 2, it is preferred that the first rod baffle 48 be formed from a band 56 which encircles the tube bundle. Struts 90 extend from each of the bands 56 generally radially, preferably along chords near a diameter of the vessel, generally parallel to the direction of the tube rows, and provide a means for attaching the bands 56 and thus the baffles and tube bundles with respect to the vessel wall. Struts 92 extend generally transversely from the bands 56 with respect to the direction of the tube rows to provide additional support of the tube bundle to enable it to withstand the forces set up in a stirred vessel when the tube bundles are employed therein. Cross braces 94 preferably connect adjacent bands 56 and extend co-rotationally around a portion of the tube bundle to better resist torquing forces.

Where the tube bundle 52 is to be used in a fermentor for the production of yeast oro bacteria it is desirable that construction of the bundle be sufficiently open to facilitate thorough cleaning between runs. Wide spacing between the individual tubes is thus desirable. To support the widely spaced tubes requires relatively large sized support rods. It can also be desirable to position the rods at highly oblique angles through the tube bundle so that the increased rod diameter brought on by the greater spacing between the tube rows is minimized. Generally speaking, where the spacing between adjacent tubes in the same row is in the range of from about 1.5D to about 2.5D, D being the outside diameter of the tubes, the spacing between adjacent rows of tubes is in the range of from about 2D to about 4D and the rods will have a diameter in the range of from about 0.5D to about D.

FIGS. 8 and 9 illustrate a preferred embodiment of the invention as employed in a fermentor.

Vessel 34, as illustrated in FIG. 8, is equipped with an agitation means including shaft 130 which is driven by drive means 139. Shaft 130 is shown fitted with two impellers, 156 and 158. Impellers 156 and 158 are constructed of discs 152 and 154, respectively, on which a plurality of blades 151 and 153, respectively, are mounted. A greater number of impellers can be employed, depending on vessel height, width, the dimensions of the heat exchange means, etc. As shown in FIG. 8, it is preferred that the bottom-most impeller be positioned in close proximity to sparger 149, to facilitate oxygen transfer in the fermentation fluid. By the term "close proximity", it is meant that the bottom-most impeller and the sparger are positioned within about $\frac{1}{8}$ to 1/10 impeller diameters from one another.

Additional impellers can be employed on shaft 130 positioned in a variety of relative orientations. For ease of mounting on stirring shaft 130, multiple impellers can be spaced equally along the shaft, with the uppermost impeller preferably being positioned at about 60 percent of the vessel height, as shown in FIG. 8 for impeller 158.

Heat exchange fluid is provided to parallel tube assemblies 1 via inlet means 30, as shown in FIG. 8. Inlet means 30 is preferably connected to a supply of heat exchange fluid by conduit 208, preferably liquid ammonia. The heat exchange fluid passes through inlet means 30. After heat exchange fluid passes through the tube assemblies 1 of the bundle, it is collected and discharged via outlet means 36. Preferably at least two baffles in the form of tube bundles 52 of parallel tube assemblies 1, are employed in the vessel 34. As illustrated in FIG. 8, each baffle comprises a bundle of parallel tubes in parallel rows. The tube assembles 1 in each baffle are typically about 25-90% of the length of the straight (generally cylindrical) portion of the vessel, not including the domed vessel heads.

A widely varied number of tube bundles can be employed, depending on the size of the tube bundles, the number of tubes per bundle, etc. Up to as many as 30 bundles per vessel can be employed, within the range of about 4 up to 24 baffles per vessel being preferred.

The blades 151 153, respectively can be mounted on the discs 152 and 154, respectively in a variety of ways, e.g., with blades 151 and 153, respectively mounted both perpendicular to the plane of the discs and on a radial projection from the vertical axis of the discs, or, alternatively, the blades 151 and 153 can be mounted on the discs 152 and 154, respectively oriented at some angle with respect to the axis of the disc. Alternatively, impeller designs other than the specific design illustrated herein, can be employed, such as, for example, axial flow impellers, marine type propellers, and the like. In a preferred embodiment, the bottom-most impeller 156 will be equipped with a plurality of blades which are oriented perpendicular to the plane of the disc, while the additional impellers other than the bottom-most impeller be of the same configuration or of other impeller types as are known in the art.

The upper limit as to impeller diameter is defined by the inner diameter of the tube bundles comprising the heat exchange means in the vessel, i.e. inside of the innermost tubes mounted on the split pipe headers. An impeller diameter which approaches this upper limit will provide the maximum amount of mixing per impeller. It is preferred that the impeller diameter not be smaller than about 10% of the total internal vessel diameter, and generally the impeller diameter will not exceed about 40% of the total internal vessel diameter. Preferably, an impeller diameter of about 20% to 35% of the total internal vessel diameter will be employed.

As shown in FIG. 8, fermentation vessel 34 is also provided with first inlet 146 and second inlet 147, as well as gas inlet 145. While vessel 34 is illustrated with the two inlets 146 and 147, all feed to the fermentor could be introduced via only one inlet means or a plurality of inlet means, wherein various feed components are separately introduced. For example, for many fermentation processes, it is desirable to introduce the nutrient media and the carbon and energy source as separate feed streams. While inlets 146 and 147 are with one discharge port each, more dispersed introduction of feed can be achieved be employing inlets having multiple discharge ports. In addition, the inlet ports can be conveniently located at various positions about the fermentation vessel, frequently being positioned as dictated by considerations of engineering expediency.

Inlet 145 is used to introduce oxygen and optionally the nitrogen source to the fermentation vessel. Gas introduced via inlet 145 enters the fermentation vessel through sparger 149. The sparger is preferably positioned symmetrically in the fermentor vessel with respect to the longitudinal axis of the fermentor vessel and has a face side containing a plurality of holes therein. Preferably, the diameter of the sparging means is no greater than the diameter of the bottom-most impeller under which the face side of the sparger is closely positioned.

As a result of the method of gas introduction, plus the location of impeller 156 in close proximity to sparger 149, as well as the position of the tube bundles, all contribute to the extremely high rate of oxygen transfer of which the inventive fermentation apparatus is capable. The fermentation vessel of the invention is capable of oxygen transfer rates in the range of at least about 300 millimoles of oxygen per liter per hour (mmol $O_2$/L/hr). In addition, the heat removal capability of the invention fermentation vessel is sufficient to remove the large amounts of heat produced by the fermentation, which large amounts of heat are generated as a result of the high levels of oxygen made available to the fermentation broth. Thus, heat removal on the order of at least about 36 Kcal/liter/hour are possible with fermentation apparatus constructed in accordance with the present invention.

Fermentation vessel 34 is also equipped with means for removing ferment, i.e. port 148. When fermentation is carried out in continuous mode, continuous or intermittent withdrawal of ferment can be accomplished via port 148 while fresh nutrients are provided via inlets 146, 147 and 145.

Fermentation vessel 34 is further equipped with at least one means for degassing foam, e.g., a foam breaker, such as for example the foam breaker disclosed by Hunt in U.S. Pat. No. 4,373,024, assigned to Phillips Petroleum Company, or the assembly of elements 162, 164 and 166 forming the degassing means as illustrated in FIG. 8. Cones 162 are mounted on shaft 164 which is rotated by drive means 166. The impact of foaming ferment with rotating cones 162 causes disruption of the foam and causes liquid to return to the main part of the fermentation vessel while gas released from the foam exits the fermentor via line 168. While at least one foam breaker will be employed on the invention fermentation vessel, sufficient foam breaking capacity to handle the amount of foam anticipated from a given fermentation process can be provided by an appropriate number of foam breakers located about the dome portion of the fermentation vessel.

The fermentation aerobic aqueous processes requires molecular oxygen which is supplied by a molecular oxygen-containing gas such as air, oxygen-enriched air, or even substantially pure molecular oxygen, so as to maintain the ferment with an partial pressure effective to assist the microorganism species in growing or in biochemically converting substrate in a thriving fashion. By using an oxygenated hydrocarbon substrate, the total oxygen requirements for growth or substrate conversion of the microorganism can be reduced from the requirements when a paraffin is used.

The pressure employed for the microbial fermentation step can range widely. Typical pressures are in the range of about 0 to 150 psig, presently preferably about 0 to 60 psig, more preferably 35 to 40 psig, as a balance of equipment and operating costs versus oxygen solubility achieved. Greater than atmospheric pressure are advantageous in that such pressures do tend to increase the dissolved oxygen concentration in the aqueous ferment, which in turn can help increase cellular growth rates. At the same time this is counterbalanced by the fact that high pressures do increase equipment and operating costs.

The refrigerant is usually under sufficient pressure and flowrate to result in a vapor/liquid exhaust from the tube bundle at a temperature in the range of 30°–50° F. (0° C–10° C.).

Reasonalbe variations from and modifications of this invention as disclosed herein are contemplated to be within the scope of patent protection desired and sought.

That which is claimed is:

1. An apparatus comprising,
   (a) a vessel capable of containing a liquid and a gas, said vessel being partly defined by a sidewall which defines a generally cylindrical inside surface, said vessel having a longitudinal axis about which the sidewall is generally symmetrically positioned;
   (b) a pipe mounted in said vessel, said pipe having a sidewall;
   (c) a partition mounted in said pipe dividing the inside of the pipe into a first chamber and a second chamber;
   (d) a first tubular member having a first end attached to the sidewall of the pipe and a second end having a closure thereon;
   (e) a second tubular member having a first end attached to the partition and a second end spaced apart from the end closure of the first tubular member, the second tubular member extending inside of the first tubular member; wherein a flow path is formed from the first chamber, through the second tubular member, through an annulus between the second tubular member and the first tubular member, and into the second chamber;
   (f) a fluid inlet means extending through the sidewall of the vessel and connected to the first chamber wherein the fluid inlet means comprises a feed pipe extending through the sidewall of the vessel and a curved supply pipe extending generally circumferentially around the inside of the vessel at a position spaced apart from the sidewall of the vessel and connected to the first chamber by a riser feed;
   (g) a fluid outlet means extending through the sidewall of the first vessel and connected to the second chamber wherein the fluid outlet means comprises a first exhaust pipe extending through the sidewall of the vessel connected to a curved collection pipe extending generally circumferentially around the inside of the vessel at a position spaced apart from the sidewall of the vessel and a riser exhaust pipe connecting the second chamber to the curved collection pipe.

2. Apparatus as in claim 1 further comprising a plurality of said pipes mounted in said vessel, said plurality of pipes being generally radially oriented with respect to the longitudinal axis of the vessel, each of said generally radially oriented pipes having an inner end and an outer end;
   a plurality of first tubular members and a plurality of second tubular members mounted to each of said pipes;
   riser feed pipes connecting each of said generally radially positioned pipes with the curved collection pipe.

3. Apparatus as in claim 2 wherein the curved supply pipe is connected to an inside end of portion of each generally radially positioned pipe by a riser feed pipe and an outside end portion of each generally radially positioned pipe is connected to the curved collection pipe by a riser exhaust pipe.

4. Apparatus as in claim 4 further comprising a liquid ammonia supply means communicating with the fluid inlet means.

5. Apparatus as in claim 1 further comprising
   a gas compressor positioned to draw fluid from the fluid outlet means;
   a condenser positioned to cool the exhaust from the gas compressor;
   a conduit means connecting the gas compressor with the condenser;
   and a conduit means connecting the condenser with the fluid inlet means.

6. Apparatus as in claim 2 further comprising pluralities of spacers positioned in the annulus between the first tubular member and the second tubular member to maintain the first tubular member and the second tubular member in spaced relationship.

7. Apparatus as in claim 6 wherein the vessel has an upper end and a lower end and is generally vertically positioned having an upper portion and lower portion; wherein the fluid inlet means and the fluid outlet means are positioned in a lower portion of the vessel, the first tubular member and second tubular member extend from the fluid inlet means and the fluid outlet means toward the upper end portion of the vessel.

8. An apparatus as in claim 7 further comprising an agitation means comprising
   (a) a shaft centrally positioned within said vessel and co-axially aligned with the longitudinal axis of the vessel;
   (b) drive means attached to said shaft and
   (c) a plurality of impellers mounted on said shaft, wherein the diameter of said impellers is no greater than the diameter of an unobstructed zone defined by the tubular members most adjacent the inner end of the radially positioned pipe.

9. Apparatus as in claim 8 further comprising inle means for the introduction of nutrient media and carbon can energy source into said vessel;
   inlet means for the introduction of gas into said vessel;
   outlet means for the removal of ferment from the lower end portion of said vessel; and
   means for degassing foam mounted in an upper portion of the vessel and positioned on the outer perimeter thereof.

10. A process comprising
   (a) introducing a heat exchange fluid into a vessel through an inlet means extending through the vessel wall;
   (b) distributing the heat exchange fluid from the inlet means into a plurality of first heat exchange tubes each having a first end and a second end and connected by the first end to the inlet means;
   (c) flowing the first heat exchange fluid from the first end to the second end of the plurality of first heat exchange tubes;
   (d) emitting the first heat exchange fluid from the second end of the first plurality of heat exchange tubes and into the first end of a second plurality of heat exchange tubes each concentrically positioned around a heat exchange tube of the first plurality and flowing the heat exchange fluid from the first end of the second plurality of heat exchange tubes, along a plurality of annuli defined between the first heat exchange tubes and the second heat exchange tubes, to a second end of the second heat exchange tubes;
   (e) discharging the heat exchange fluid from the second end of the second heat exchange tubes and collecting the discharged heat exchange fluid in an exhaust means which extends through the vessel wall; and
   (f) withdrawing the heat exchange fluid from the vessel through the exhaust means.

11. A process as in claim 10 wherein the heat exchange fluid comprises liquid ammonia and the heat exchange fluid withdrawn from the vessel comprises a mixture of ammonia liquid and ammonia vapor.

12. A process as in claim 11 further comprising condensing the ammonia vapor and introducing the thus condensed ammonia vapor into the inlet means.

13. A process as in claim 11 wherein a distance of at least one outer second heat exchange tube diameter separates the outer surfaces of the tube of the second plurality;
   said process further comprising circulating a fermentation broth across the outer surface of the tubes of the second plurality of heat exchange tubes.

14. A process as in claim 13 wherein the plurality of first heat exchange tubes and second heat exchange tubes are generally radially aligned with respect to a longitudinal axis of the vessel; wherein the vessel contains a multiplicity of said pluralities of such tubes.

15. A process as in claim 11 wherein the mixture is at a temperature of between about 30° F. and about 50° F.

* * * * *

UNITED STATES PATENT AND TRADEMARK OFFICE
CERTIFICATE OF CORRECTION

PATENT NO. : 4,882,283
DATED : November 21, 1989
INVENTOR(S) : Cecil C. Gentry

It is certified that error appears in the above-identified patent and that said Letters Patent is hereby corrected as shown below:

Column 9, line 6, please insert the following paragraphs

--riser feed pipes connecting each of said generally radially positioned pipes with the curved supply pipe; and--

--riser exhaust pipes connecting each of the generally radially positioned pipes with the curved--

Column 9, line 15, delete "4" and insert --3--.

Column 9, line 27, delete "2" and insert --3--.

Column 9, line 52, delete "line" and insert --inlet--.

Column 9, line 54, delete "can" and insert --and--.

Signed and Sealed this

Sixth Day of November, 1990

*Attest:*

HARRY F. MANBECK, JR.

*Attesting Officer*　　　　*Commissioner of Patents and Trademarks*

UNITED STATES PATENT AND TRADEMARK OFFICE
CERTIFICATE OF CORRECTION

PATENT NO. : 4,882,283
DATED : November 21, 1989
INVENTOR(S) : Cecil C. Gentry

It is certified that error appears in the above-identified patent and that said Letters Patent is hereby corrected as shown below:

Column 9, lines 7 and 8, after "curved", please delete "collection pipe.", and insert therefor ---supply pipe; and---

Column 9, after line 8, please add the following paragraph: ---riser exhaust pipes connecting each of the generally radially positioned pipes with the curved collection pipe.---

Column 9, line 15, delete "4" and insert ---3---.

Column 9, line 27, delete "2" and insert ---3---.

Column 9, line 52, delete "inle" and insert ---inlet---.

Column 9, line 54, delete "can" and insert ---and---.

This certificate supersedes Certificate of Correction issued November 6, 1990.

Signed and Sealed this

Twenty-fourth Day of December, 1991

Attest:

HARRY F. MANBECK, JR.

*Attesting Officer*  *Commissioner of Patents and Trademarks*